United States Patent [19]
Kring

[11] Patent Number: 6,105,418
[45] Date of Patent: Aug. 22, 2000

[54] CONSTANT HEAD FLOW UNIT

[76] Inventor: Timothy D. Kring, 3610 Chartwell Dr., Suwanee, Ga. 30024

[21] Appl. No.: 09/179,059

[22] Filed: Oct. 26, 1998

[51] Int. Cl.[7] .............................. G01N 15/08; G01N 5/02
[52] U.S. Cl. ..................................... 73/38; 73/73
[58] Field of Search ........................................... 73/38, 73

[56] References Cited

U.S. PATENT DOCUMENTS 5,269,184  12/1993  Nishida ....................................... 73/73

*Primary Examiner*—Hezron Williams
*Assistant Examiner*—Jay L. Politzer
*Attorney, Agent, or Firm*—William B. Noll

[57] ABSTRACT

On-site percolation testing apparatus comprising a constant head flow unit disposed within a generally cylindrical, percolation chamber to be positioned within the in-ground test site. The constant head flow unit includes a J-shaped conduit for intermittently delivering water from a predetermined supply of water to the chamber. A first end of the conduit extends up from and out of the chamber in direct communication with the water supply. A second end thereof, disposed within the chamber, includes an automatic shut-off valve to control the flow of water through the conduit into the chamber. Cooperating with the shut-off valve is a floating member positioned to move up and down as the water level changes. As the floating member moves down it contacts the shut-off valve and opens same to release water into the chamber. With the water rising, the floating member moves out of contact with the valve allowing the water pressure of the incoming water to again close the valve. This process will be repeated a number of times during the test. However, by the use of the constant head flow unit hereof, a relatively constant level of water is maintained in the chamber to thereby give the system more reliability.

6 Claims, 3 Drawing Sheets

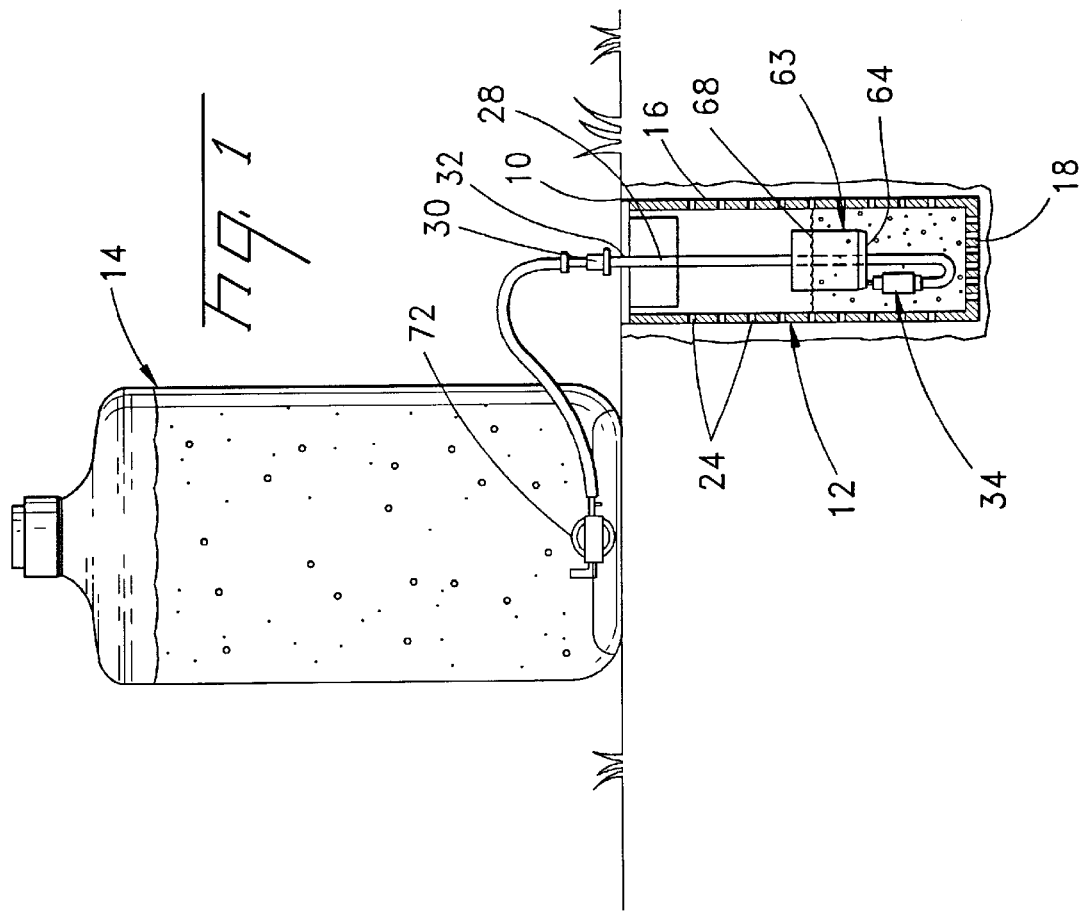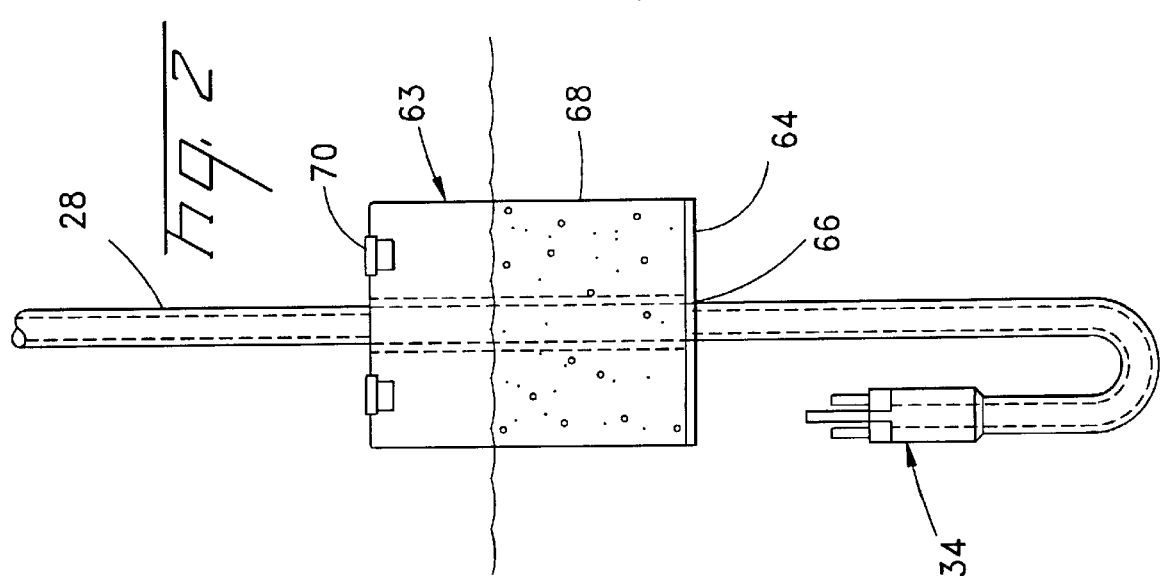

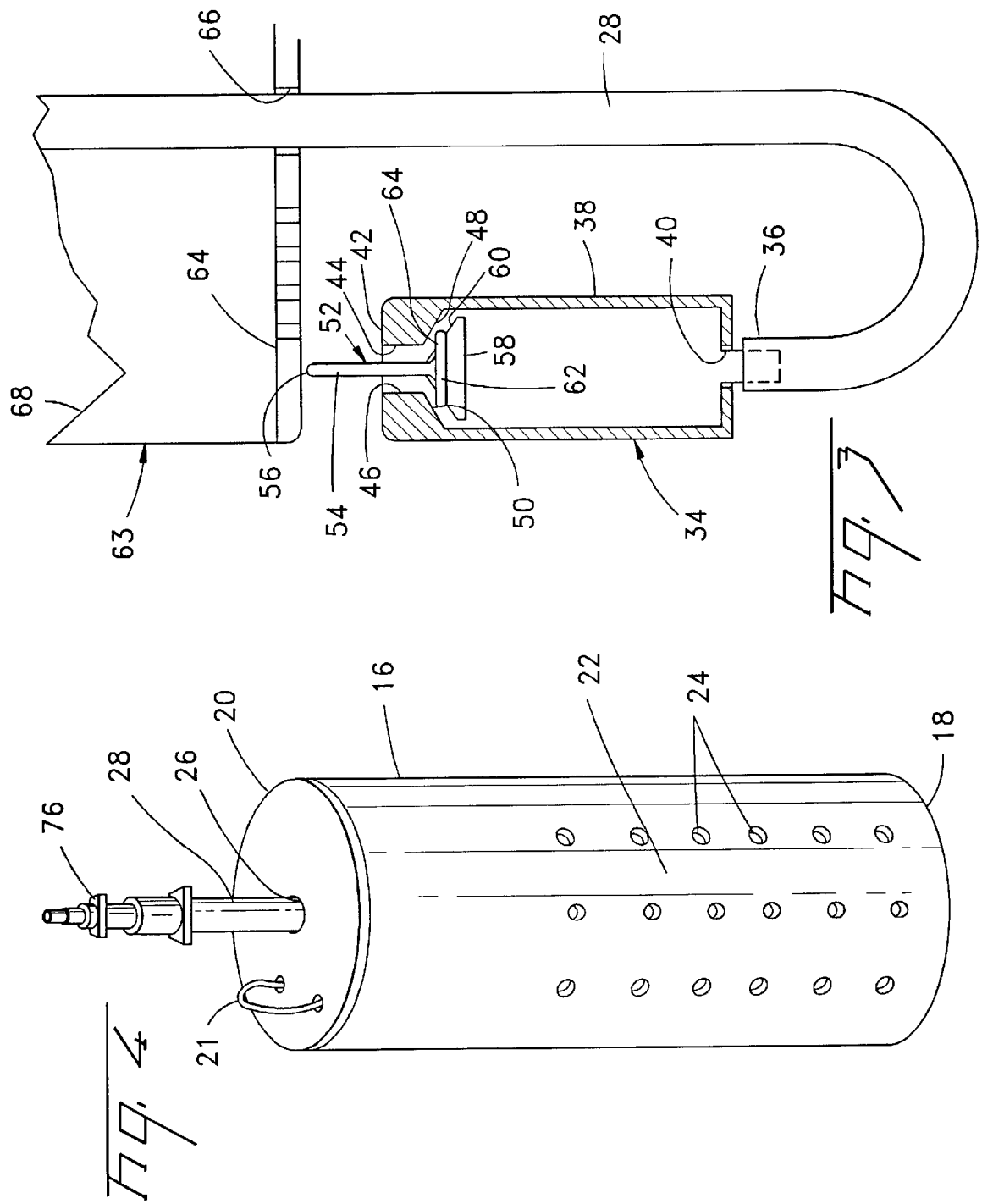

CONSTANT HEAD FLOW UNIT

FIELD OF THE INVENTION

This invention is directed to the field of apparatus for determining soil percolation measurements by the use of a constant head flow unit to ensure reliability.

BACKGROUND OF THE INVENTION

The present invention relates to a user friendly, accurate system for performing soil percolation tests to determine the suitability of a parcel of land to support a structure, and its related water run-off capabilities, constructed on such parcel.

The use of percolation tests in soil testing, such as to determine proper sewage disposal systems is well known in the art. Basically, the testing requires a time determination for the water to be absorbed into the soil at a specific location. This is normally accomplished by providing a test hole, filling the hole with a quantity of water, floating an indicator on the fluid surface and timing the period for the indicator to drop a certain distance, or conversely, recording the various distances dropped with respect to a fixed time period. This timing may take a relatively long period and the cost of performing such a simple percolation test may be relatively expensive.

This simple process has been made more difficult by certain health standards that require that the water remain in the test hole for a predetermined period before the actual percolation test is performed. This time is termed a saturation time or soak time and a percolation test is performed prior to a standard for saturation is, in many cases, held to be invalid. Obviously, if personnel is required to continually monitor this dual test situation, the cost of testing becomes extremely high.

Recognizing the need for better and more accurate systems for performing soil percolation tests, the prior art, as reflected in the following U.S. patents, has developed various means in attempts to meet these challenges, namely:

a.) U.S. Pat. No. 3,945,247, to Anderson, teaches apparatus for performing soil percolation tests, where such apparatus includes a housing member having upper and lower portions, with the lower portion adapted for insertion into a soil percolation test opening in the soil. A depth gauging member is mounted within the housing member for transitional movement with respect to the housing member. The soil percolation test opening is filled to a predetermined level with water and the depth gauging member translated to a position indicative of the water level. After a predetermined time the water level in the percolation test opening falls due to absorption by the soil and the depth gauging member is translated into a new position indicative of the new water level. Calibration markings on the housing permit a direct reading of the amount by which the depth gauging member has been translated, which corresponds to the amount of the water level in the percolation test opening has fallen. The housing member is also provided with a timer and with facilities for introducing water into the percolation test opening.

b.) U.S. Pat. No. 4,099,406, to Fulkerson, relates to a device for the automatic determination and recordation of rates of fluid absorption in soils, including a plurality of conductive probes which are positioned at various levels with regard to a provided water level such that the water level drops, and the time to accomplish the drop is recorded. The device provides a pair of timing and time recording devices interconnected with the probes such that the two individual time sequences may be recorded.

c.) U.S. Pat. No. 4,182,157, to Fink, discloses percolation testing apparatus comprising an elongated guide rod having one end to be driven into the bottom of a test hole for simple and sole support of the rod. Mounted within is a gauge rod slidable by means of guide brackets on the latter and a scale strip is attached to the upper end of the gauge rod for vertical movement relative to a reference marker supported adjustably upon the upper portion of the said guide rod. A float is connected to the lower level end of the gauge rod for floating movement vertically in the test hole to move the scale strip relative to the reference marker which is stationary on the guide rod.

d.) U.S. Pat. No. 4,341,110, to Block, teaches an apparatus for automatically recording the rate of fluid absorption of soil and includes three subsystems which may be easily assembled on site. During a test procedure the rate of dissent of a float is recorded on a tape by a timer controlled marker.

e.) U.S. Pat. No. 4,561,290 to Jewell, discloses a float valve assembly for soil percolation measurements. The float valve assembly, integral with a water supply system, responds to changes in a predetermined water level inside a test bore to regulate water flow through the float valve into the bore to maintain this water level. The float valve assembly can be positioned at different depths below the ground level by suspension at the lower end of a premarked flexible hose hanging freely inside the test bore. The float valve housing is open at its lower end, so that water around it in the test bore can raise the float within to throttle the water flowing down through a reducer at the end of the hose and directly above the float. After an initial transient stage, the water in the test bore percolates away from the test bore through the soil around it at a steady rate, measured to obtain the steady state percolation rate at that site at the selected depth.

f.) U.S. Pat. No. 4,829,817, to Kozlowski, relates to a soil percolation testing system. The system includes a threaded shaft; a plurality of marking discs that can be selectively positioned along the shaft at predetermined graduations; a positioning brace that overlies the shaft for securing the shaft in vertical alignment; a mounting disc affixed near a base end of the shaft and becomes flush with the soil when the shaft is inserted into a percolation test hole; and a receiving disc near a top end of the shaft for receiving the positioning brace as it straddles the test hole. In using the device, the person administering the test adjusts the marking discs along the shaft to predetermined graduations; secures the device within a percolation test hole; fills the hole with water, observes from a remote distance the descent of the column of water within the hole; observes the formation of meniscus around a first marking disc below which the column of water has descended; and records the time variable when a wave appears on the surface of the water resulting from the snap of meniscus as the column of water descends further below the first and subsequent marking discs.

g.) U.S. Pat. No. 4,984,447, to Phillips, teaches a soil percolation testing apparatus. The apparatus has a hollow shaft for insertion into a test hole and includes vertically adjustable wedging blades slidable and T-tracks on the shaft for centering alignment in the test hole. A hand pump evacuates water from the test hole to a predetermined null point whereupon movement of a float and float rod supported and guided within the shaft over a finite period of time will yield a direct percolation absorption rate.

While the foregoing offer some solutions to the problem of determining percolation rates of selected soil sites, none appear as user friendly and simple as provided by the present invention. The manner by which such goals are achieved herein will become apparent to those skilled in the art from the following specification, particularly when read in conjunction with the accompanying drawings.

SUMMARY OF THE INVENTION

Invention relates to an apparatus for performing in-ground percolation site tests on a parcel of land having a pre-bored hole sized to receive a constant head flow unit placed therein. The apparatus comprises a constant head flow unit and a predetermined water supply, such as a container or tank. The constant head flow unit includes a water percolation chamber having holes thereabout to allow water to flow therefrom. Within the chamber is a J-shaped conduit for intermittantly delivering water from the water supply to the chamber. A first end of the conduit extends out of the chamber in communication with the water supply. A second, or upturned end, disposed within the chamber, includes an automatic shut-off valve to control the flow of water and maintain same at a relatively constant level within the chamber. Cooperating with the shut-off valve is a floating member sidably engaging a vertical portion of the conduit The floating member includes a generally planar base positioned to activate the shut-off valve. Finally, the water supply means in a preferred form includes a calibrated tubular member that features a manually depressible valve to catch, maintain, and measure the water level of the water supply, thereby providing an easy means to measure the flow rate of water, and hence the percolation rate of the soil.

Accordingly, an object of his invention is to provide an effective system for conducting an on-site percolation test by the use of apparatus utilizing a constant head flow unit.

Another object hereof is the provision of a percolation testing system that virtually runs itself without extensive manhour support.

A further object of this invention is its reliability through the use of an essentially constant water level during the performance of the test.

Still another object hereof is the provision of a unique dipstick volume gauge which allows for instant measurements of how much has flowed into the on-site percolation hole.

These and other objects will become more apparent to those skilled in the art from the description which follows.

BRIEF DESCRIPTION OF THE DRAWINGS

FIG. 1 is a simplified plan view of the apparatus according to this invention, showing the constant head flow unit thereof positioned within a pre-bored percolation test site.

FIG. 2 is an enlarged plan view showing certain details of the constant head flow unit of this invention.

FIG. 3 is a further enlarged, partially sectioned plan view of an automatic water supply valve forming part of the constant head flow unit for the present invention.

FIG. 4 is a perspective view of the percolation chamber, according to this invention, where such chamber houses the constant head flow unit of FIGS 2 and 3.

DETAILED DESCRIPTION OF PREFERRED EMBODIMENT

Figure 5:
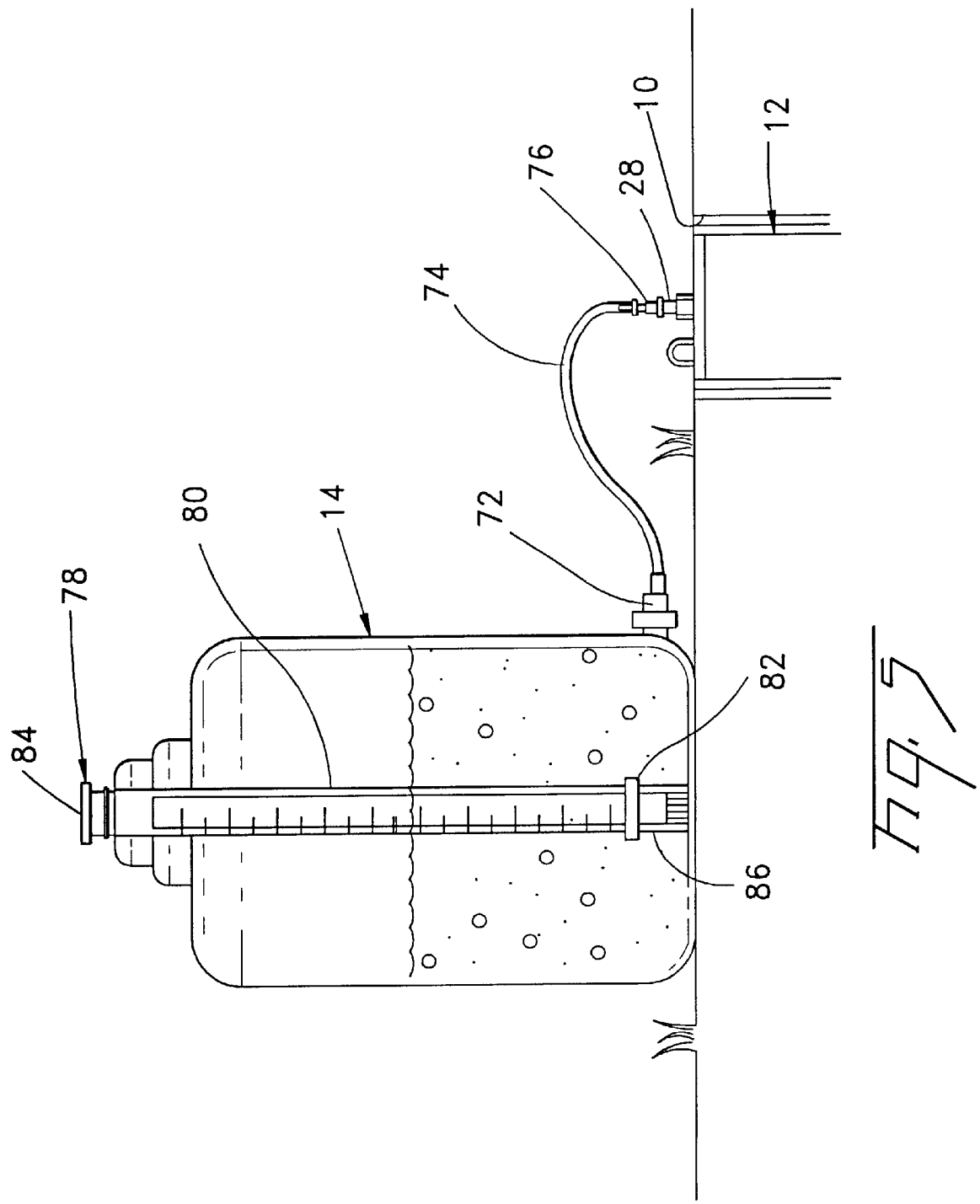
FIG. 5 is a plan view of an exemplary water supply chamber for the system hereof, where the chamber includes a calibrated cylindrical member for periodically determining the rate of water supplied to the system of this invention.

The present invention is directed to apparatus for performing in-ground percolation site tests on a parcel of land to determine its suitability for sustaining a water run-off system, such as a septic system, for example. The apparatus is illustrated in the several Figures, where like reference numerals represent like components or features throughout the several views.

As best illustrated in FIG. 1, and by way of additional background, a percolation test site is generally prepared by digging a hole, such as by an appropriate auger boring device, as known in the art. A practical dimension for such a hole 10 may be approximately six inches in diameter and thirty six inches in depth. However, depending upon soil conditions, and/or governmental regulations, the diameter and depth may vary.

Turning now to the apparatus of this invention, an operable system is illustrated in FIG. 1, where the apparatus includes a constant head flow unit 12 and a water supply system 14 to feed water to the constant head flow unit 12. The constant head flow unit 12 preferably comprises a hollow cylindrical percolation chamber 16 (FIGS. 1 and 4), having a circular base 18, a removable circular top 20, and a chamber side wall 22, where plural holes 24 are provided in said wall to allow water to pass therethrough, as hereafter explained.

The circular top 20 may include a handle 21 to remove such top for maintenance purposes, etc., and features a central opening 26 for receiving a water transmitting conduit 28. Projecting through said central opening 26 is the conduit 28, configured in the form of a "J", having a first valve means 30 at the top 32 and a shut-off valve assembly 34 at the upturned end 36. The shut-off valve assembly 34, as best seen in FIG. 3, may comprise an open ended cylindrical member 38, opened at the bottom 40 and in fluid communication with the upturned end 36. In a preferred arrangement, the top 42 includes a central opening 44 characterized by a uniform diameter portion 46 and a diverging portion 48 with slanted wall 50. Positioned to move up and down within the central opening 44 is a T-configured, reversely oriented, plunger member 52. The plunger member 52 includes a plunger arm 54 with a free end 56, and an opposite end 58. The opposite end 58 features a tapered face 60, where the angle of the face 60 is comparable to the slanted wall 50. To facilitate sealing of the cylindrical member 38, when the plunger member 52 is in the uppermost position, tapered face 60 may include an annular slot 62 for receiving a sealing O-ring 64.

To effect opening of the shut-off valve assembly 34, by depression of the plunger member 52, a free floating member 63 is positioned about conduit 28. The floating member 63 is characterized by at least a planar bottom plate 64, such as fabricated from plastic, sized to freely slide along conduit 28 within a central opening 66. As best seen in FIG. 2, the plate 64 may include a body portion 68 formed of light weight materials, such as cork or a closed cell foam, along with calibrated weights 70, where desired, to give sufficient weight to the floating member 63 to depress the plunger member 52 against the incoming water pressure, see FIG. 3.

The operation of the system hereof requires a predetermined quantity of water to feed the system. FIGS. 1 and 5 illustrate an exemplary water tank 14 in the form of a 6-gallon water tank for example. The tank 14 may include an open/close valve 72 to release the water through hose 74 to the connector 76 into conduit 28. As best seen in FIG. 5, the system hereof may include a unique dipstick volume gauge 78. In a preferred design, the gauge 78 comprises a calibrated cylindrical tubular member 80 open at its respective ends 82, 84. The lower end 82 may include a spring biased valve plunger 86, which allows, through depression of said plunger 86, to fill the tubular member 80 to the level of the water within the tank 14. In other words, to readily determine such level of water in the tank at any given time internal, the user merely has to push down on the tubular member 80, which in turn depresses the valve plunger 86, whereby water flows into the tubular member 80 up to the level of the water in the tank. Thereafter, one merely has to remove the tubular member 80 from the tank 14 and read the water level therein at the calibrated level. This, for example, may reflect a first reading after a timed interval of operation.

To operate the system in performing a soil percolation test, the water tank 14 is filled to the prescribed level of water and the constant head flow unit 12 is positioned within a pre-bored hole 10, where the soil is to be tested. If required, a preliminary and separate quantity of water is put into the hole 10 to initiate the percolation test. Thereafter, the open/close valve 72 is opened to allow water to fill the conduit 28 and close the plunger member 52. At this position, the floating member 63 is floating above the plunger member 52. However, as the water in the hole 10 begins to percolate into the soil, the remaining water begins to recede allowing the floating member 63 to drop into contact with free end 56. As the floating member 63 continues to drop, the weight of the floating member 63 pushes against the plunger arm 54 which allows water to pass around the tapered face 60 through opening 44 into the chamber formed by side wall 22. With this fresh supply of water, the floating member 63 rises allowing the plunger member 52 to move upward and close the opening 44. With continued percolation, the process is repeated. By this simple operation, a relatively constant level or head of water is maintained in the hole 10 to thereby assure a more reliable reading on the percolation rate of the soil. For such reading of the percolation rate, the dipstick volume gauge 78 may be used, as noted above.

It is understood that variations and modifications may be made to the apparatus hereof, particularly by those skilled in the art. Accordingly, no limitations should be imposed thereon except as set forth in the accompanying claims.

What is claimed is:

1. Apparatus for performing in-ground percolation site tests on a parcel of land having a pre-bored hole sized to receive a constant head flow unit therewithin, said apparatus comprising:

a.) a constant head flow unit including a water percolation chamber having plural holes to allow water to flow therefrom;

i.) a J-shaped conduit for intermittantly delivering water to said chamber, where a first end extends above said chamber, and a second end is within said chamber, said second end including an automatic shut-off valve to control the flow of water into said chamber, said automatic shut-off valve including a generally cylindrical chamber having a first opening in communication with said J-shaped conduit, and a second opening receiving a floating valve piston, said piston including a valve stem extending from within said cylindrical chamber through said second opening;

ii.) a floating member, having a central opening for engaging said J-shaped conduit in a sliding relationship, and positioned to move up and down within said chamber, where said floating member includes a generally planar base positioned to open said automatic shut-off valve in a down position, whereby as said floating member moves down into contact with said valve stem, said valve stem is depressed to allow water from said cylindrical chamber to flow into said percolation chamber; and, b.) a predetermined water supply to deliver water to said first end, including manual means to measure the water delivered by said water supply.

2. The testing apparatus according to claim 1, wherein said manual means includes a calibrated tubular member that may be manually retrieved from said water supply for inspection.

3. The testing apparatus according to claim 2, wherein said calibrated tubular member includes a valve plunger to manually access and maintain a measured quantity of the water of said water supply.

4. The testing apparatus according to claim 1, wherein said valve stem includes a head portion for abutting engagement with said second opening, said head portion including an O-ring for sealing contact with said second opening.

5. The testing apparatus according to claim 1, wherein said floating member includes removably replaceable weights to adjust the floating capabilities of said member.

6. The testing apparatus according to claim 1, wherein said floating member further includes a light weight body mounted to said planar base.

* * * * *